(12) United States Patent
Mathisen et al.

(10) Patent No.: US 8,906,047 B2
(45) Date of Patent: *Dec. 9, 2014

(54) MESH IMPLANT FOR USE IN RECONSTRUCTION OF SOFT TISSUE DEFECTS

(75) Inventors: Torbjörn Mathisen, Älvsjö (SE); Henrik Magnusson, Uppsala (SE)

(73) Assignee: Novus Scientific AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/312,007

(22) Filed: Dec. 6, 2011

(65) Prior Publication Data

US 2012/0083807 A1 Apr. 5, 2012

Related U.S. Application Data

(63) Continuation of application No. 11/472,563, filed on Jun. 22, 2006, now Pat. No. 8,083,755.

(51) Int. Cl.
*A61B 17/08* (2006.01)
*A61F 2/00* (2006.01)

(52) U.S. Cl.
CPC .................................. *A61F 2/0063* (2013.01)
USPC .......................................... 606/151; 606/213

(58) Field of Classification Search
USPC ................ 606/152–200, 213, 110–112, 151; 623/11; 424/422–426; 604/304–308
See application file for complete search history.

(56) References Cited

U.S. PATENT DOCUMENTS

| | | |
|---|---|---|
| 4,865,031 A | 9/1989 | O'Keeffe |
| 4,916,193 A | 4/1990 | Tang et al. |
| 4,983,184 A | 1/1991 | Steinemann |
| 5,147,400 A | 9/1992 | Kaplan et al. |
| 5,686,090 A * | 11/1997 | Schilder et al. ............... 424/423 |
| 5,733,337 A * | 3/1998 | Carr, Jr. et al. ............... 435/325 |
| 6,162,962 A * | 12/2000 | Hinsch et al. ............. 623/11.11 |
| 6,235,869 B1 | 5/2001 | Roby et al. |
| 6,268,544 B1 | 7/2001 | Court et al. |

(Continued)

FOREIGN PATENT DOCUMENTS

| | | |
|---|---|---|
| CN | 1169277 A | 1/1998 |
| EP | 0 797 962 B2 | 10/1997 |

(Continued)

OTHER PUBLICATIONS

U.S. Appl. No. 13/081,998, filed Apr. 7, 2011, Mathisen et al.

(Continued)

*Primary Examiner* — Gregory Anderson
*Assistant Examiner* — Christina Lauer
(74) *Attorney, Agent, or Firm* — Foley & Lardner LLP

(57) ABSTRACT

The present invention relates to a resorbable polymeric mesh implant, that is intended to be used in the reconstruction of soft tissue defects. The mesh implant comprises at least a first and a second material, wherein the second material is substantially degraded at a later point in time than the first material following the time of implantation. The mesh implant is adapted to have a predetermined modulus of elasticity that gradually is decreased until the mesh implant is completely degraded and subsequently resorbed. Due to the gradual decrease in the modulus of elasticity of the inventive mesh implant, the regenerating tissue may gradually take over the load applied to the tissue defect area.

13 Claims, 2 Drawing Sheets

A
B
C

(56) References Cited

U.S. PATENT DOCUMENTS

| | | | |
|---|---|---|---|
| 6,319,264 B1* | 11/2001 | Tormala et al. | 606/151 |
| 6,514,515 B1* | 2/2003 | Williams | 424/424 |
| 7,749,273 B2 | 7/2010 | Cauthen, III et al. | |
| 8,016,841 B2 | 9/2011 | Magnusson et al. | |
| 2002/0042128 A1 | 4/2002 | Bowlin et al. | |
| 2002/0062152 A1 | 5/2002 | Dauner et al. | |
| 2003/0082148 A1* | 5/2003 | Ludwig et al. | 424/93.7 |
| 2003/0193104 A1 | 10/2003 | Melican et al. | |
| 2004/0138762 A1 | 7/2004 | Therin et al. | |
| 2005/0070930 A1 | 3/2005 | Kammerer | |
| 2005/0113849 A1 | 5/2005 | Popadiuk et al. | |
| 2005/0222591 A1 | 10/2005 | Gingras et al. | |
| 2005/0267325 A1 | 12/2005 | Bouchier et al. | |
| 2005/0288797 A1 | 12/2005 | Howland | |
| 2006/0083767 A1 | 4/2006 | Deusch et al. | |
| 2006/0142786 A1 | 6/2006 | Mathisen et al. | |
| 2007/0142698 A1 | 6/2007 | Bourne et al. | |
| 2008/0119848 A1 | 5/2008 | Shalaby et al. | |
| 2008/0306494 A1 | 12/2008 | Magnusson et al. | |
| 2009/0024151 A1 | 1/2009 | Shalaby et al. | |
| 2009/0024162 A1 | 1/2009 | Shalaby et al. | |
| 2011/0066168 A1 | 3/2011 | Magnusson et al. | |
| 2011/0112561 A1 | 5/2011 | Mathisen et al. | |

FOREIGN PATENT DOCUMENTS

| | | |
|---|---|---|
| EP | 1 252 905 A2 | 10/2002 |
| EP | 1 674 048 A1 | 6/2006 |
| JP | 2-167156 A | 6/1990 |
| JP | 4-61863 A | 2/1992 |
| JP | 10-24054 A | 1/1998 |
| WO | WO 03/092758 A1 | 11/2003 |
| WO | WO 2004/050133 A2 | 6/2004 |
| WO | WO 2006/116000 A2 | 11/2006 |
| WO | WO 2007/014995 A2 | 2/2007 |

OTHER PUBLICATIONS

"Standard Test Method for Bursting Strength of Textiles—Constant-Rate-of-Traverse (CRT) Ball Burst Test," ASTM—International, Designation: D 3787-01.

U. Klinge et al., "Abnormal Collagen I to III Distribution in the Skin of Patients with Incisional Hernia.", European Surgical Research, 2000, pp. 43-48.

K. Junge et al., "Elasticity of the anterior abdominal wall and impact for reparation of incisional hernias using mesh implants", May 2001, pp. 113-118.

D. Roylance, "Introduction to Composite Materials," Mar. 24, 2000, pp. 1-7, Dept. of Materials Science and Engineering, MIT, Cambridge, MA.

K. Van de Velde et al., "Biopolymers: overview of several properties and consequences on their applications," Sep. 11, 2001, pp. 433-442, Polymer Testing 21, Elsevier Science Ltd., Zwijnaarde, Belgium.

W. H. de Jong et al., "Late tissue reactions and degradation of biodegradable polylactide implants. An experimental study in rats," National Institute of Public Health and the Environment (Bilthoven, The Netherlands), Report No. 605148 006, Jun. 1996, pp. 1-38.

T. Mathisen et al., US PTO Office Action, U.S. Appl. No. 11/019,534, dated Feb. 11, 2008, 10 pgs.

T. Mathisen et al., US PTO Office Action, U.S. Appl. No. 11/019,534, dated Jun. 20, 2007, 12 pgs.

T. Mathisen et al. US PTO Final Office Action, U.S. Appl. No. 11/019,534, dated Aug. 5, 2010, 14 pgs.

T. Mathisen et al., US PTO Office Action, U.S. Appl. No. 11/019,534, dated Aug. 28, 2008, 10 pgs.

T. Mathisen et al., US PTO Office Action, U.S. Appl. No. 11/019,534, dated Nov. 16, 2006, 12 pgs.

T. Mathisen et al., US PTO Office Action, U.S. Appl. No. 11/019,534, dated Aug. 27, 2009, 12 pgs.

H. Magnusson et al., US PTO Final Office Action, U.S. Appl. No. 11/808,563, dated Feb. 28, 2011, 10 pgs.

T. Mathisen et al., US Examiner's Answer, U.S. Appl. No. 11/019,534, dated Feb. 17, 2011, 12 pgs.

H. Magnusson et al., US PTO Office Action, U.S. Appl. No. 11/808,563, dated Jun. 16, 2010, 19 pgs.

T. Mathisen et al., US PTO Final Office Action, U.S. Appl. No. 11/808,563, dated Jan. 3, 2011, 11 pgs.

H. Magnusson et al., US PTO Notice of Allowance, U.S. Appl. No. 11/808,563, dated Jul. 27, 2011, 14 pgs.

T. Mathisen et al., US PTO Final Office Action, U.S. Appl. No. 11/472,563, dated Oct. 28, 2009, 13 pgs.

T. Mathisen et al., US PTO Final Office Action, U.S. Appl. No. 11/472,563, dated Dec. 23, 2009, 12 pgs.

T. Mathisen et al., US PTO Office Action, U.S. Appl. No. 11/472,563, dated Nov. 12, 2008, 14 pgs.

T. Mathisen et al., US PTO Final Office Action, U.S. Appl. No. 11/472,563, dated Jun. 25, 2009, 12 pgs.

T. Mathisen et al., US PTO Notice of Allowance, U.S. Appl. No. 11/472,563, dated Oct. 20, 2011, 15 pgs.

H. Magnusson et al., US PTO Non-Final Office Action, U.S. Appl. No. 12/952,723, dated Feb. 13, 2012, 17 pgs.

T. Mathisen et al., US PTO Non-Final Office Action, U.S. Appl. No. 13/081,998, dated Aug. 2, 2012, 17 pgs.

T. Mathisen et al., US PTO Non-Final Office Action, U.S. Appl. No. 13/004,530, dated Jul. 3, 2012, 22 pgs.

Henrik Magnusson et al., US PTO Notice of Allowance, U.S. Appl. No. 12/952,723, dated Jul. 25, 2012, 10 pgs.

US PTO Office Action, U.S. Appl. No. 13/617,742, Jun. 6, 2013, 14 pgs.

T. Mathisen et al., US PTO Final Office Action, U.S. Appl. No. 13/004,530, dated Jan. 2, 2013, (18 pgs.).

H. Magnusson et al., US PTO Office Action, U.S. Appl. No. 13/617,742, dated Jan. 2, 2013, (12 pgs.).

T. Mathisen et al., U.S. PTO Decision on Appeal, U.S. Appl. No. 11/019,534, dated Oct. 8, 2013, (8 pgs.).

T. Mathisen et al., US PTO Office Action, U.S. Appl. No. 13/081,998, dated Mar. 28, 2013, (15 pgs.).

T. Mathisen et al., USPTO "Decision on Request for Rehearing", U.S. Appl. No. 11/019,534, dated Mar. 24, 2014, (6 pgs.).

T. Mathisen et al., USPTO Office Action, U.S. Appl. No. 13/004,530, dated May 6, 2014, (20 pgs.).

Partial European Search Report, Nov. 19, 2007, 3 pages.

Chinese Office Action, Sep. 15, 2011, 12 pages.

Australian Patent Examination Report No. 1, Nov. 5, 2012, 3 pages.

Japanese Office Action, Nov. 13, 2012, 2 pages.

T. Mathisen et al., UPSTO Final Office Action U.S. Appl. No. 13/004,530, dated Aug. 15, 2014, (18 pgs).

* cited by examiner

MESH IMPLANT FOR USE IN RECONSTRUCTION OF SOFT TISSUE DEFECTS

TECHNICAL FIELD

The present invention relates to a resorbable polymeric mesh implant and a polymeric mesh implant kit. The mesh implant, as well as the kit, is intended to be used in the reconstruction of soft tissue defects. The mesh implant comprises at least a first material and a second material, wherein the second material is substantially degraded at a later point in time than the first material, following the time of implantation of the mesh implant. The mesh implant is adapted to have a substantially constant modulus of elasticity during a short initial time period after implantation, after which period the modulus of elasticity is decreased until the mesh implant substantially looses its mechanical properties and subsequently is completely degraded and absorbed by the body. Due to the gradual decrease in the modulus of elasticity of the inventive mesh implant, the regenerating tissue may gradually take over the load applied to the tissue defect area until the mesh implant is completely resorbed. With the inventive mesh implant there is no longer a need for inert, non-resorbable, long term supporting structures.

BACKGROUND ART

Within the field of surgical repair of soft tissue defects, use is often made of a mesh implant made of a non-resorbable material that is inserted to cover the area of the tissue defect. The mesh implant is used in order to support the regenerating tissue, and in, e.g. hernia defects, it works by mechanical closure of the defect and by inducing a strong scar fibrous tissue around the mesh implant. Such a mesh implant is most often made of various plastics, which are known to stay biostable and safe for a number of years after implantation. However, introducing a foreign material into the human or animal body is most often accompanied with side effects like migration, chronic inflammation, risk of infection etc. The introduction of a relatively large plastic body is also likely to induce a foreign body-reaction caused by the body's immune defence system. As a result, the mesh implant may crumple up and loose its tissue supporting function.

The above mentioned mesh implants are in particular used in the repair of defects in the abdominal wall, which may be a result from trauma, tumour resection, prolapse or hernia.

A hernia is an abnormal protrusion of a peritoneal-lined sac through the musculoaponeurotic covering of the abdomen, the most common site for a hernia being the groin. Types of hernia are, among others, inguinal hernia or a femoral hernia, hiatal hernia, umbilical hernia and incisional hernia, the latter being a hernia that pushes through a past surgical incision or operation.

One suggested theory in the field is that some patients, due to collagen metabolic disorders, have a genetic predisposition for developing recurrent hernias. An altered ratio of collagen types I and III in these patients, with an increase in collagen type III, is believed to reduce the mechanical strength of connective tissues. The decreased tensile strength of collagen type III plays a key role in the development of incisional hernias, see KLINGE, U, et al. Abnormal collagen I to III distribution in the skin of patients with incisional hernia. *Eur Surg Res.* 2000, vol. 32, no. 1, p. 43-48.

It is in particular in the cases of large or recurrent hernias that the surgical repair or herniorrhaphy makes use of an inert, non-resorbable mesh implant, as described above. The mesh implant is inserted to cover the area of the abdominal wall defect without sewing together the surrounding muscles. This can be done under local or general anesthesia using a laparoscope or an open incision technique.

Among the laparoscopic techniques used, are the trans-abdominal pre-peritoneal (TAPP) technique and the totally extra-peritoneal (TEP) technique. With the TAPP technique, the pre-peritoneal space is accessed from the abdominal cavity, whereupon the mesh implant is placed between the peritoneum and the transversalis fascia. With the TEP technique, the mesh implant is again placed in the retroperitoneal space, but the space is accessed without violating the abdominal cavity. An open and minimal invasive technique is the Lichtenstein hernia repair technique, in which the upper edge of the mesh implant is attached to the outer side of the internal oblique and the lower edge of the mesh implant is attached to the aponeurotic tissue covering the pubis.

Another open minimal invasive technique is the mesh-plug technique comprising attaching a mesh implant, as described above in reference to the Lichtenstein technique, but also inserting a plug pushing the peritoneum in a direction towards the abdominal cavity.

The mesh implant, inserted with any of the above described techniques, is used in order to support the regenerating tissue with minimal tension. It works by mechanical closure of the defect in the abdominal wall and by inducing a strong scar tissue around the mesh implant fibres. The commercially available hernia mesh implants are often made of various, inert, non-resorbable polymeric materials, typically polypropylene, and suffers from the same disadvantages, as described above in connection with mesh implants used for reconstruction of soft tissue defects in general. However, implantation of large pieces of mesh implants in the abdominal wall cavity, also leads to considerable restriction thereof. In a study performed by Junge et al, JUNGE, K, et al. Elasticity of the anterior abdominal wall and impact for reparation of incisional hernias using mesh implants. *Hernia*. 2001, no. 5, p. 113-118., the elasticity of the abdominal wall was measured and compared to that of commercially available non-resorbable hernia mesh implants. It was assumed that the flexibility of the abdominal wall is restricted by extensive implantation of large mesh implants, the more so if the mesh implants are integrated into scar tissue.

In addition, the non-physiological stretching capability of the mesh implants contrast with the highly elastic abdominal wall and can give rise to shearing forces, favouring increased local remodelling and thus recurrence at the margin. It was concluded that mesh implants used for repairing inscisional hernia should have an elasticity of at least 25% in vertical stretching and 15% in the horizontal stretching when subjected to a tensile strength of 16 N/cm, in order to achieve almost physiological properties.

The progress within hernia repair mesh implant development, as well as in the development of mesh implants for the use of reconstruction of soft tissue defects in general, has been towards mesh implants with less mass in order to minimize foreign body reactions, and larger pore sizes, which on one hand reduce the mass of the mesh implant and on the other facilitate ingrowth of tissue.

U.S. Pat. No. 6,319,264 B (TÖRMÄLÄ) 20.11.2001 describes a porous, flexible and fibrous hernia mesh, which is intended to be implanted close to hernia defects. The mesh comprises two functional layers, wherein the first layer is a rapidly degradable polymer layer facing the fascia, and wherein the second layer is a more slowly degradable polymer layer. The first polymer layer has a fast resorption profile, approximately 14 days, said first layer promotes scar tissue formation due to inflammatory reactions induced by the polymer degradation and due to the porous structure of the first layer.

The second polymer layer has a longer resorption time, approximately 6 months, and thus supports the area until the scar tissue is strong enough to resist pressure and prevent recurrent hernia formation. An optional third dense, thin, bioabsorbable layer is described, which prevents agents that could cause tissue to tissue adhesion from moving from the hernia area through the mesh and onto the surrounding tissue during the first weeks after the operation. The mesh described in U.S. Pat. No. 6,319,264 acts as a temporary support until connective scar tissue has strengthened enough and can replace the mesh, when the second layer finally degrades.

However, U.S. Pat. No. 6,319,264 is silent as to the load situation found over the tissue defect area and to the modulus of elasticity of the hernia mesh. In the above described mesh, only the second layer is designed to support the tissue during the regenerative phase. The mesh material is by the body regarded as an inert material, in that no major changes in mechanical properties are observed until degradation has reached to such a point where the material starts to crack with a more or less catastrophic change in mechanical properties taking place.

The complex but well orchestrated sequence in wound healing starts with hemostasis and the wound is usually fully closed within 10 to 14 days. However, depending on the individual and the size of the wound, the healing sequence may be faster or slower. This is especially true if the wound is infected. Collagen remodelling and deposition is however a continuous process slowly building up the strength in the wounded tissue. Fibroblasts play a key role in the early phase of the wound-healing and are present already from day 2 or 3. The key role of the fibroblasts is to deposit new collagen into the wounded area rebuilding the extra-cellular matrix and thus repairing the wounded tissue. This first deposited collagen is most often laid down in a random non-oriented fashion and is often referred to as scar tissue. However, by stimulating the wound already during the early or acute phase of wound healing we have reason to believe that a denser and stronger collagen layer is deposited. These findings implicate that the surgical mesh used for soft tissue reconstruction should possess properties that would allow the mesh to become more compliant with the surrounding tissue during the early phase of wound healing and a continuous increase in compliance could be visualized after the remodelling phase starts. After the acute wound-healing phase is over, the wound is often remodelled, i.e. the first deposited collagen is replaced by a more structurally rigid collagen. During this remodelling period, the newly formed tissue will undergo several phases, during which the tissue gradually becomes more specific to support the various stress situations found in the area. Following the teachings of Junge et al, a mesh implant used for reconstruction of soft tissue defects, should have an elasticity that is compatible with the elasticity of the surrounding tissue, so that the flexibility of said tissue is not substantially restricted.

It is therefore believed that device compliance will play a key role in the remodelling sequence of the first deposited collagen. But to our surprise we have also found that meshes used for soft tissue repair and which alter their mechanical properties in the very early phase of the wound healing sequence rather than in the remodelling phase of the wound, may stimulate gross infiltration of collagen into the knitted mesh construct. This early infiltration of collagen may play a crucial role in the strength of the wound at a later stage. It appears that a polymeric mesh for reconstruction of soft tissue defects should be so designed that it will allow for early stimulation of the newly deposited tissue. This can be accomplished by allowing an early change in the modulus of the implant so that it gradually become more and more compliant to the surrounding tissue.

The inventors of the present invention therefore suggest that a device used to temporarily support the tissue defect in the area where the tissue is exposed to various stress situations should be so designed as to allow for an early change in the modulus of the implant, best expressed as an increased elongation, thus allowing an early stimulation of the deposited collagen in the wound area followed by a gradual change in compliance of the implant allowing the newly formed tissue to gradually take over the load during the remodelling phase and thus build up the strength and compliance needed to take over the full load once the support from the temporarily implanted device is lost.

DISCLOSURE OF THE INVENTION

The object of the present invention is therefore to provide a resorbable mesh implant for use in reconstruction of soft tissue defects, the mechanical properties of which stimulates the ingrowing, regenerating tissue, and at the meantime allowing the regenerated tissue to gradually take over the load found in the tissue defect area until the mesh implant substantially looses it mechanical properties and subsequently is completely resorbed. Another object of the present invention is to provide a polymeric mesh implant kit.

These objects are achieved by the present invention according to the preambles of the independent claims and provided with the features according to the characterizing portions of the independent claims. Preferred embodiments of the present invention are set forth in the dependent claims.

DETAILED DESCRIPTION OF PREFERRED EMBODIMENTS

Figure 1:
FIG. 1 schematically shows an embodiment of the present invention, wherein the mesh implant comprises two materials A and B, FIG. 2 schematically shows an alternative embodiment of the present invention, wherein the mesh implant comprises three materials A-C, FIG. 3 schematically shows a cross section of one structural design of the embodiment shown in FIG. 3.

An embodiment of the present invention is shown in FIG. 1, wherein the mesh implant comprises two resorbable polymeric materials, material A and material B. Material A is characterized by a time of substantial degradation, $t_A$, and a modulus of elasticity, $E_A$. Consequently, material B is characterized by a time of substantial degradation, $t_B$, and a modulus of elasticity, $E_B$. Material B is substantially degraded at a later point in time, following the time of implantation of the mesh implant, than material A, i.e. $t_A<t_B$. The time of substantial degradation herein being defined as the point in time at which the material substantially change its mechanical properties. One could also define the time of substantial degradation as the point in time at which the mechanical integrity of the material no longer provide the mesh implant with mechanical properties that contribute to the object of the inventive mesh implant. For instance, the mechanical properties of the material may have declined at the time of substantial degradation, so that the mechanical strength of the material is less than approximately 30% of its initial strength.

The modulus of elasticity of material A is higher than the modulus of elasticity of material B, i.e. $E_A > E_B$, and consequently, the elongation of material A is lower than the elongation of material B. It is here understood that $E_A$ and $E_B$ is the modulus of elasticity of the respective material in the present configuration. Thus, a material A will, for example, generally have a lower $E_A$ if the material A is designed as having a perforated structure than if the same material A exhibits a homogenous structure. For the different materials of the inventive mesh implant, a modulus of elasticity is preferably within the range of 300 kPa-3 GPa. It is to be noted that the modulus of elasticity of a material need not to have the same value in all directions, thus the modulus of elasticity in for instance the vertical direction need not to be identical with the modulus of elasticity in the horizontal direction. The burst strength method as described in ASTM D 3787-1 is especially useful in characterizing mesh structures. Since modulus of elasticity can be difficult or impossible to elucidate the compliance of the implant can more preferably be given as the elongation, recalculated from the distension, at certain load values using the burst test method above.

$t_A$ is in the time range of 2 to 13 days or more preferably 3 to 9 days after the time of implantation, i.e. $t=t_0$, and $t_B$ is at least 3-18 months after the time of implantation, preferably in the time range of 6-12 months.

In the mesh implant according to the embodiment described above, material A and material B can be structurally designed as two separate perforated layers, respectively, arranged on top of each other. Also, material A and material B can be partly or fully incorporated with each other, which will be explained in further detail below. After implantation the mesh implant can be fixed with for instance suitable sutures, staples, fixation, pins, adhesives or the like. In some applications of the implant, the pressure from the surrounding tissue may be enough for initial fixation until newly regenerating tissue anchors the implant by tissue through growth.

Material A acts as an initial and temporary support during the primary wound healing time period $t=t_0-t_A$, during which $E_A$ is high and substantially constant, allowing the elongation of the mesh implant to be no more than in the range of 0 to 20%, but more preferably in the range of 0-10%.

Material A is substantially degraded at time $t_A$, leaving material B to alone carry the load applied to the tissue defect area. However, due to the significantly lower modulus of elasticity of material B, part of the load will be transferred onto the surrounding and ingrowing tissue. The mechanical stimulation of the wound area will thus stimulate the cells to deposite new extracellular matrix as well as stimulate remodelling of the existing tissue to be oriented according to the existing load pattern and gradually take over the load carried by the mesh implant during the time period of $t_A-t_B$. Thus, material B facilitates the mechanical stimulation of the surrounding tissue, e.g. aponeurotic structures, to develop the strength needed to finally take over the total load applied to the tissue defect area when the mesh implant is substantially degraded and subsequently completely resorbed.

Figure 4:
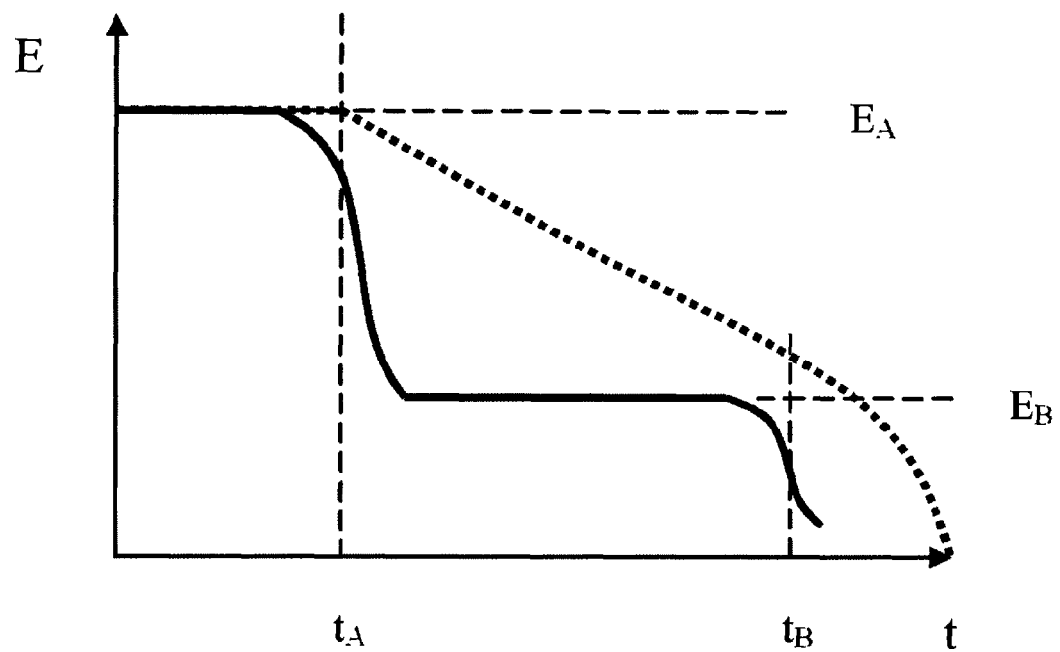
FIG. 4 shows the modulus of elasticity of the mesh implant shown in FIG. 1 as a function of time (not to scale)

FIG. 4 shows the modulus of elasticity, E, of the mesh implant shown in FIG. 1 comprising material A and material B, as a function of time, t. During $t=t_0-t_A$, material A practically carries the entire load over the tissue defect area due to the higher modulus of elasticity of said material. E is substantially constant with respect to time and thus corresponds to $E_A$ during said time period. As described above, E is during the time period of $t=t_0-t_A$ high enough not to allow any substantial elongation of the mesh implant. A more or less sudden increase in elongation is observed around $t=t_A$ when the mechanical properties of material A starts to change as a consequence of the ongoing degradation. During $t=t_A-t_B$, $E=E_B$ since the load over the tissue defect area is carried by material B alone, as described above. Preferably, $E_B$ corresponds to an elongation of the mesh implant that is compatible with the elasticity of the surrounding tissue, so that the flexibility of said tissue is not substantially restricted.

Figure 3:

In an alternative embodiment of the inventive mesh implant, the mesh implant comprises a third resorbable polymeric material C, characterised by $t_C$ and $E_C$ with $t_A < t_B < t_C$, and $E_A > E_B > E_C$. Also here it is understood that $E_C$ is the modulus of elasticity of material C in its present configuration, as explained above. Thus, the mesh implant comprises in the alternative embodiment three materials A, B and C. In said alternative embodiment the materials A through C can be structurally designed as three separate perforated layers, arranged on top of each other, as seen in FIG. 3. The materials A through C can also be partly or fully incorporated with each other, as explained in further detail below. Two of the materials can be partly or fully incorporated with each other, but not the third, wherein any combination of materials may be possible.

When the mesh implant according to the alternative embodiment is inserted into the body (see discussion above that refers to implantation of the mesh implant according to the embodiment comprising material A and B) material A, due to its high modulus of elasticity, acts as an initial and temporary support during the primary wound healing time period $t=t_0-t_A$. Material A is substantially degraded at time $t_A$, at which time material A substantially looses its mechanical properties, as described above. Material B, due to its higher modulus of elasticity than material C, then carries the load applied to the tissue defect area, but due to the lower modulus of elasticity of material B than of material A, part of the load will be transferred onto the surrounding and ingrowing tissue. At time $t_B$ material B is substantially degraded, leaving material C to carry the load applied to the soft tissue defect area. Due to the even lower modulus of elasticity of material C, further load will be transferred to the surrounding tissue. As described above, material B and material C thus allow a biomechanical stimulation on the tissue, that will enable it to regenerate and remodel into a load bearing tissue, e.g. aponeurotic structures, tendons or ligaments, that gradually will take over the load carried by the mesh implant during the time period of $t_A-t_C$.

Figure 2:
Figure 5:
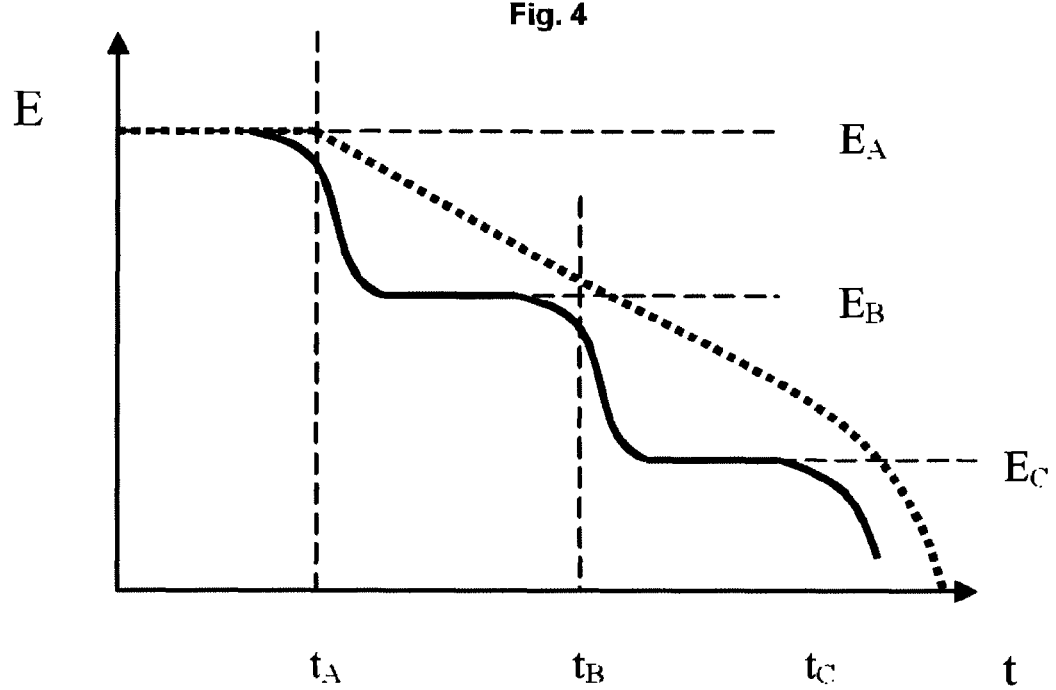
FIG. 5 shows the modulus of elasticity of the mesh implant shown in FIGS. 2 and 3 as a function of time (not to scale).

E as a function of time for the alternative embodiment shown in FIGS. 2 and 3, is shown graphically in FIG. 5. $t_A$ is, as in the embodiment shown in FIG. 1, approximately 2 to 13 days or more preferably 3 to 9 days, and $t_C$ is at least 3-18 months after the time of implantation, preferably in the time range of 6-12 months. $t_B$ can thus be anywhere between 14 days and 18 months, as long as $t_A < t_B < t_C$. In said alternative embodiment, material C acts as the last substantially degraded material of the mesh implant and $E_C$ preferably corresponds to an elongation of the mesh implant that is compatible to the elasticity of the surrounding tissue, so that the flexibility of said tissue is not substantially restricted. Thus, $E_B$ can have a predetermined value anywhere between $E_A$ and $E_C$.

The mesh implant according to the present invention, thus strives to imitate the ideal E versus t situation, shown as a dotted line in FIGS. 4 and 5, of a resorbable mesh implant used to temporarily support soft tissue defects during reconstruction thereof. In the ideal situation, E of the mesh implant is during the primary wound healing time period substantially constant and high enough not to allow any substantial elongation of the mesh implant, whereupon the mesh implant is degraded with a gradual decrease in E so that the newly formed tissue may gradually take over the load applied to the tissue defect area during the remodelling phase. In the ideal situation, the mesh implant thus biomechanically stimulates the surrounding tissue to build up the strength and compliance needed to take over the full load once the support from the temporarily implanted device is lost after at least 3-18 months. During the final stage of the remodelling phase, the modulus of elasticity of the mesh implant preferably corresponds to an elongation of the mesh implant that is compatible with the elasticity of the surrounding tissue, so that the flexibility of said tissue is not substantially restricted. The modulus of elasticity of various soft tissues varies over a broad range from tendons having elastic modulus around 700 MPa to very low modulus found in elastine rich tissue where modulus can be around 300 kPa. The modulus above is only approximate values due to the often non-linear behaviour of soft tissue. If the inventive mesh implant is intended to be used in the reconstruction of defects in the abdominal wall, following the teachings of Junge et al, the elasticity of the mesh implant, during the final stage of the remodelling phase, preferably corresponds to an elongation of 18-32% when subjected to a load of 16 N/cm.

Since a high modulus of elasticity of the mesh implant corresponds to a low elongation thereof, the ideal situation can just as well be described by ways of elongation of the mesh implant as a function of time. In that case the mesh implant is preferred to have a very low and substantially constant elongation during the first days of the wound healing period followed by a gradual increase in elongation. During the final stage of the remodelling phase, the mesh implant preferably has an elongation as described above.

The inventive mesh implant can thus comprise any number of materials, as long as it strives to imitate the ideal E versus t situation. However, due to manufacturing reasons, the number of materials is preferably not more than five and more preferred 3-4.

In yet an alternative embodiment of the inventive mesh, the mesh implant according to any of the above described embodiments, can comprise a further resorbable polymeric material D (not shown), which has essentially the same characteristics as material A, with respect to time of substantial degradation, $t_D$. Material D can, in fact, be the same material as material A, but present in another configuration such that $E_D$ is not equal to $E_A$. Material D is adapted to provide an extra supportive structure during $t=t_0-t_A$ and enables more ingrowth of fibrous tissue. Material D can be structurally designed as a separate perforated layer or can be partly or fully incorporated with any of the other materials of the mesh implant, see further discussion below.

The mesh implant can also be provided with still a further material E (not shown), which material E is substantially degraded approximately at the same point in time as any of the other materials present in the mesh implant, and thus in fact be the same material as any of the other said materials. Material E can be present in another configuration than that of the material with which it has approximately the same time of substantial degradation, so that $E_E$ is not equal to the modulus of elasticity of that material, or material E can have approximately the same modulus of elasticity as that material. Material E can be structurally designed as a separate perforated layer or can be partly or fully incorporated with any of the other materials of the mesh implant, see further discussion below.

Optionally a thin resorbable film (not shown) can be applied to the mesh implant, in any of the above described embodiments, in order to prevent adhesion of the mesh implant to surrounding tissues. If the mesh implant is intended to be used in the repair of abdominal wall defects, the thin film is preferably applied on the surface of the mesh implant facing towards the abdominal cavity in order to in particular prevent adhesion onto the intestines. Said film is preferably a thin hydrophilic film, for instance a carbohydrate film, with a thickness in the range of 1-300 microns, that forms a hydrogel structure when the film is brought into contact with fluids contained in the tissue.

The inventive mesh implant preferably has mechanical properties that enables it to be inserted into the body with any conventionally used technique for implantation of mesh implants used for reconstruction of soft tissue defects, for instance any of the techniques described in reference to the implantation of hernia mesh implants. A mesh implant is herein being defined as an implant device with any type of through going perforation, including pores, naturally occurring perforations or artificially created perforations, which extend from the proximal surface to the distal surface of the implant device, so that there is a communication between said proximal and distal surface. The materials of the inventive mesh implant, can be fibres made from any bioresorbable polymer, copolymer, polymer blend or polymer composite, or can be combined assorted bioresorbable polymer parts, as long as the materials have suitable predetermined times of substantial degradation and modulus of elasticity, so that when the materials are combined, the inventive mesh implant strives to imitate the ideal E versus t situation of a resorbable mesh implant used to temporarily support soft tissue defects during reconstruction, as described above.

Non-limiting examples of such synthetic resorbable materials are various combinations of the monomers glycolide, lactide and all stereoismers therof, trimethylene carbonate, epsilon-caprolactone, dioxanone or dioxepanone. Depending on the desired mechanical properties and the choice of manufacturing method, several of the homopolymers or copolymers containing two or more of the above-mentioned monomers can be used to manufacture the mesh structure. Yet other examples of synthetic resorbable polymers that can be utilized are various aliphatic polyurethanes, such as polyureaurethanes, polyesterurethanes and polycarbonateurethanes, and also materials such as polyphosphazenes or polyorthoesters.

The materials of the inventive mesh implant can have a woven or knitted structure with pores of a suitable pore size, or can have a non-woven, for instance electro-spun, structure, wherein the (electro-spun) non-woven structure can further be furnished with man made through and through holes. When two or more materials are incorporated with each other, fibres of said materials, respectively, can be jointly woven, knitted or non-woven into the same suitable structure. Also various materials can be spun into fibres which are braided, twisted into a multifilament produced from two or more materials, which multifilament is woven, knitted or non-woven into said suitable structure. It is understood that any combination of fibers in the form of monofilament, filament bundles, multifilament or braided or twisted multifilament can be combined into the desired structure. Moreover anyone of the fiberstructures mentioned above may be individually coated as well as the final product. Preferably however, material A, and D, has, or is incorporated into, a porous, woven or knitted structure with a pore size preferably in the range of 50-4000 microns, or a non-woven, for instance electro-spun structure, since a porous structure with a pore size in the above mentioned range, or a non-woven structure, enable for fibroblasts and other connective tissue cells to grow into the pores, or into the non-woven structure, during the primary wound healing period. However, material A and D, need not to have, or be incorporated into, the same structural design, thus material A can have, or be incorporated into, a woven or knitted structure while material D has, or is incorporated into, a non-woven structure and vice versa.

The last substantially degraded material of the inventive mesh implant, preferably has, or is incorporated into, a porous woven or knitted structure, with a pore size preferably in the range of 0.5-4 mm, more preferred 1-3 mm, in order to minimize the mass of the mesh implant as well as maximizing the tissue supporting effect of said last substantially degraded material.

Any other material can have, or be incorporated into, either a porous woven or knitted structure, or a non-woven, for instance electro-spun structure. If said materials have, or are incorporated into, a porous woven or knitted structure it is preferred, however not mandatory, that also this structure has a pore size in the range of 0.5-4 mm, more preferred 1-3 mm for reasons as described above.

The mesh implant can also be provided with trough going macro-pores, that extend from the proximal surface to the distal surface of the mesh implant, in order to further facilitate the communication between the proximal and distal surfaces of the mesh implant.

Shown schematically in FIG. 3, is a cross section of a possible structural design of the inventive mesh implant comprising materials A, B and C, wherein material A has a non-woven structure on top of material B and C, which are incorporated with each other into a woven or knitted, porous structure. However, it is pointed out that the structural design shown in FIG. 3, is not preferred to the other possible structural designs of the inventive mesh implant.

The area weight of the inventive mesh as described above is preferably 20 to 300 g/m2 or more preferably 30 to 150 g/m2 in its dry state.

The inventive mesh can further comprise bioactive or therapeutic substances naturally present in humans or of foreign origin. These substances include, but are not limited to, proteins, polypeptides, peptides, nucleic acids, carbohydrates, lipids or any combinations thereof. Especially considered are growth factors, such as PDGF, TGF or FGF, or components of the naturally occurring extracellular matrix, including cytokines, fibronectins, collagens, and proteoglycans such as but not limited to hyaluronic acid. Therapeutic substances that are considered include, but are not limited to, antibiotic drugs and pain relieving substances. Bioactive or therapeutic substances of human or foreign origin can be entrapped within the porous structure of the implant or incorporated through covalent or other chemical or physical bonding, in an active state or as precursors to be activated upon any physical or chemical stimuli or modification.

The present invention also refers to a polymeric mesh implant kit. The kit comprises at least a first and a second material, wherein the modulus of elasticity of the second material is lower than the modulus of elasticity of the first material and wherein the second material is substantially degraded at a later point in time than the first material, however any number of the above mentioned materials can be present in the kit. The materials are provided in the kit as separate structurally designed layers and/or as materials fully or partly incorporated with each other, wherein any combination of materials is possible, by means of any of the above described ways. Each material has a predetermined modulus of elasticity in its present configuration, as defined above, and a predetermined time of substantial degradation, as defined above. Thus, the user of the kit can combine any number of materials into a polymeric mesh implant, as defined above and that strives to imitate the ideal E versus t situation described above with reference to FIGS. 4 and 5, that is tailored for each individual patient and for said patients specific needs, depending on the nature of the soft tissue defect to be repaired. At least one of the materials preferably has a time of substantial degradation within the time range of 2 to 13 or more preferably 3 to 9 days, and preferably has a predetermined modulus of elasticity that does not allow an elongation of the mesh implant, once combined, to be no more than in the range of 0-20%, preferably no more than in the range of 0-10%. At least one of the materials preferably has a time of substantial degradation within the time range of 3-18 months, preferably 6-12 months, and preferably has a modulus of elasticity that corresponds to an elongation of the mesh implant, once combined, that is compatible with the elasticity of the surrounding tissue, so that the flexibility of said tissue is not substantially restricted. As described above, the materials can have a porous, woven or knitted, or a non-woven, for instance electro-spun structure, wherein the (electro-spun) non-woven structure can further be furnished with man made through and through holes. At least one of the materials, or at least one combination of materials, can be provided with a thin resorbable film, preferably a thin hydrophilic film as described above, in order to prevent adhesion of the mesh implant, once combined, onto surrounding tissue. Said film can also be provided in the kit as a separate item and be combined with the selected materials, so that the mesh implant, once combined, is provided with said film for the above mentioned reason. Preferably, at least one of the materials of the kit that have a time of substantial degradation within the time range of 2 to 13 days or more preferably 3 to 9 days, has a porous structure with a pore size in the range of 50-4000 microns or has a non-woven, for instance electro-spun structure, for reasons as described above. Preferably at least one of the materials of the kit that have a time of substantial degradation within the time range of 3-18 months, has a porous structure with a pore size in the range of 0.5-4 mm microns, more preferred 1-3 mm, for reasons as described above. Further, at least one of the materials, or at least one combination of materials, of the kit can comprise bioactive or therapeutic substances naturally present in humans or of foreign origin, as described above.

However, it is understood that the skilled person is capable of choosing suitable materials, as defined above, in order to construe a polymeric mesh implant that is tailored for each individual patient and for said patients specific needs, depending on the nature of the soft tissue defect to be repaired, without having at hand the inventive kit. Therefore, the present invention also encompass the tailoring of a specific polymeric mesh implant for the specific soft tissue defect to be reconstructed, by choosing and combining suitable materials.

It will be understood that the invention is not restricted to the above described exemplifying embodiments thereof and that several modifications are conceivable within the scope of the following claims.

Example 1

Two knitted mesh structures, both composed of different co-knitted resorbable mono-multifilament constructions, was implanted into the abdominal wall of 12 Sprague-Dawley rats together with two commercially available meshes, polypropylene and polyethylene terephthalate, indicated for hernia repair. The resorbable knitted meshes were made from 50/50% and 35/65% glycolide/ε-caprolactone monofilaments and lactide/e-caprolactone/trimethylene-carbonate multifilaments respectively. The area weight of the meshes was 125 g/m2 respective 168 g/m2 and the max burst load was measured to 206 N respective 224 N according to ASTM D 3787-1. Elongation, measured at 16 N/cm, was 5% for both meshes. The mesh was subjected to in vitro degradation in a phosphate buffer solution at 37° C. to study the effect of the fast degrading monofilament material made from glycolide/ε-caprolactone on the overall mechanical properties of the mesh construct. After 6 days, about 50% of the strength was lost in the fast degrading monofilament and after 7 to 8 days little or no contribution to the overall mechanics of the mesh comes from the fast degrading glycolide/e-caprolactone monofilament. The mechanics was fully taken over by the slower degrading lactide/e-caprolactone/trimethylene-carbonate multifilament resulting in a max burst strength in the range 175 to 220 N after 10 and up to 28 days with a slight difference between the two meshes. The elongation at 16 N/cm was measured to 5 to 7% in the time span 0 to 6 days and thereafter started to increase to 15 respective 25% after 15 days and thereafter a slight decrease to 14 respective 22% after 28 days.

In comparison, the polypropylene and polyethylene terephthalate mesh respectively showed a max burst load of about 180 N for both meshes and an elongation at 16 N/cm of 7% respective 12%. These values are constant over the time period 0 to 28 days.

Implantation was performed with EtO sterilized samples of both resorbable and inert polypropylene mesh. The rectus abdominis muscle sheath was opened and the muscle was moved laterally. The mesh structure was inserted outside the peritoneum without injuring the peritoneal membrane. The rectus abdominus muscle was slipped back to cover the implant and a suture was placed in the muscle sheath to secure the position of the implant. The animals was euthanized after 6 weeks and the implant with surrounding tissue were removed and fixated in buffered formaldehyde before histology specimens were prepared and stained with van Gieson stain.

For both the polypropylene and polyethylene terephthalate controls a typical foreign body response was observed around each of the fibers with very little or no collagen infiltration.

For the resorbable mesh, the fast degrading fibers originating from the glycolide/ε-caprolactone were substantially degraded, in agreement with the in-vitro observation above, but with less expressed inflammatory reaction relative the polypropylene mesh. The most remarkable finding is the fine network of collagen between the multifilament bundles. The deposition and infiltration of collagen is thought to origin from the increased mechanical stimulation of the tissue when the polymeric mesh gradually looses its strength. Stimulation from early release of degradation products from the fiber may also be a contributing factor for the integration of collagen into the multifilament fiber bundles.

The invention claimed is:

1. A resorbable polymeric mesh implant whose implant configuration varies over time after implantation for use in reconstruction of soft tissue, wherein the resorbable polymeric mesh implant comprises:
   at least a first material and a second material,
   wherein the second material is substantially degraded at a later point in time than the first material,
   wherein the modulus of elasticity of the mesh implant is initially substantially constant and equal to the modulus of elasticity of the first material following a time of implantation and until said first material is substantially degraded,
   wherein the modulus of elasticity of the mesh implant substantially decreases after the first material is substantially degraded,
   wherein the modulus of elasticity of the mesh implant is such that, before the first material is substantially degraded, an elongation of the mesh implant is in a range of 0 to 20% when subjected to a load of 16 N/cm,
   wherein the elongation of the mesh implant is in a range of 18 to 32%, when subjected to a load of 16 N/cm, after the first material has substantially degraded.

2. A resorbable polymeric mesh implant according to claim 1, wherein the mesh implant is configured for use in reconstruction of soft tissue defects.

3. A resorbable polymeric mesh implant according to claim 1, wherein the mesh implant further comprises a third material that is substantially degraded at a later point in time than the second material, wherein the modulus of elasticity of the mesh implant is substantially equal to a modulus of elasticity of the third material in the implant configuration after the second material is substantially degraded.

4. A resorbable polymeric mesh implant according to claim 1, wherein the last substantially degraded material has a modulus of elasticity in the implant configuration that is compatible with the elasticity of surrounding tissue so that a flexibility of said tissue is not substantially restricted.

5. A resorbable polymeric mesh implant according to claim 1, wherein a last substantially degraded material is substantially degraded at a point in time within a time range of 3-18 months following implantation.

6. A resorbable polymeric mesh implant according to claim 1, wherein materials are chosen in order to construct a mesh implant that is tailored for a specific soft tissue to be reconstructed.

7. A resorbable polymeric mesh implant according to claim 1, wherein the mesh implant is provided with a resorbable film in order to prevent adhesion of the mesh implant to surrounding tissue.

8. A resorbable polymeric mesh implant according to claim 7, wherein the resorbable film is a hydrophilic carbohydrate film.

9. A resorbable polymeric mesh implant according to claim 1, wherein the first material and/or the second material has a porous structure with a pore size in the range of 50-4000 microns.

10. A resorbable polymeric mesh implant according to claim 1, wherein the first material and/or the second material has or is incorporated into a non-woven structure.

11. A resorbable polymeric mesh implant according to claim 1, wherein the last substantially degraded material has a pore size in the range of 0.5-4 mm.

12. A resorbable polymeric mesh implant according to claim 1, wherein the modulus of elasticity of the mesh implant is such that, before the first material is substantially degraded, the elongation of the mesh implant is in a range of 0 to 10%.

13. A resorbable polymeric mesh implant according to claim 1, wherein the first material is substantially degraded at a point in time within a time range of 2-13 days following implantation.

* * * * *